US006777189B2

(12) United States Patent
Wei et al.

(10) Patent No.: US 6,777,189 B2
(45) Date of Patent: Aug. 17, 2004

(54) NUCLEIC ACID ANALYSIS USING NON-TEMPLATED NUCLEOTIDE ADDITION

(75) Inventors: Dong Wei, Philadelphia, PA (US); Danielle Bishop, Daly City, CA (US)

(73) Assignee: Applera Corporation, Foster City, CA (US)

( * ) Notice: Subject to any disclaimer, the term of this patent is extended or adjusted under 35 U.S.C. 154(b) by 11 days.

(21) Appl. No.: 10/109,104

(22) Filed: Mar. 27, 2002

(65) Prior Publication Data

US 2002/0142342 A1 Oct. 3, 2002

Related U.S. Application Data

(60) Provisional application No. 60/280,603, filed on Mar. 30, 2001.

(51) Int. Cl.[7] ............................ C12Q 1/68; C12Q 1/48; C12P 19/34; C07H 21/04

(52) U.S. Cl. ............................ 435/6; 435/15; 435/91.1; 536/23.1; 536/24.3; 536/24.33; 536/25.32

(58) Field of Search .......................... 435/6, 91.1, 91.2, 435/15; 536/23.1, 24.33, 24.3, 25.32

(56) References Cited

U.S. PATENT DOCUMENTS

2002/0006617 A1 * 1/2002 Fan et al. ...................... 435/6

FOREIGN PATENT DOCUMENTS

WO WO 95/00669 A1 1/1995
WO WO 98/42867 A1 * 10/1998

OTHER PUBLICATIONS

Bulyk et al. Quantifying DNA–protein interactions by double–stranded DNA arrays. Nature Biotechnology, vol. 17, pp. 573–577, Jun. 1999.*

Clark, James M., "Novel Non–Templated Nucleotide Addition Reactions Catalyzed by Procaryotic and Eucaryotic DNA Polymerases," *Nucleic Acids Research*, vol. 16, No. 20, pp. 9677–9686, 1988.

Magnuson, et al., "Substrate Nucleotide–Determined Non–Templated Addition of Adenine by Taq DNA Polymerase: Implications for PCR–Based Genotyping and Cloning," *BioTechniques*, vol. 21, No. 4, pp. 700–709, Oct. 1996.

Smith, et al., "Approach to Genotyping Errors Caused by Nontemplated Nucleotide Addition by Taq DNA merase," *Genome Research*, vol. 5, No. 3, pp. 312–317, Oct. 1995.

Short Technical Reports, "Modulation of Non–Templated Nucleotide Addition by Taq DNA Polymerase: Primer Modifications that Facilitate Genotyping," *BioTechniques*, 20(6), pp. 1004–1010, Jun. 1996.

International Search Report dated Jun. 11, 2002 in PCT/US02/09482.

* cited by examiner

*Primary Examiner*—Kenneth R. Horlick
*Assistant Examiner*—Cynthia Wilder
(74) *Attorney, Agent, or Firm*—Scott R. Bortner; Andrew K. Finn

(57) ABSTRACT

One embodiment of the invention is a method of producing an oligonucleotide extended by a single nucleotide base. An oligonucleotide and an extension terminating nucleotide are mixed with an enzyme having terminal transferase activity. The reaction produces an oligonucleotide extended by a single base. The extended oligonucleotide may be used as a size standard for single base extension reactions. Another embodiment of the invention is a method of producing a mixture of oligonucleotides extended by different single bases. An oligonucleotide, a first extension terminating nucleotide, and a second extension terminating nucleotide are mixed with an enzyme having terminal transferase activity. The first and second extension terminating nucleotides comprise different nucleotide bases and are labeled with different labels. The identity of the different extension terminating nucleotides (and hence the extended oligonucleotides) may be ascertained by reference to the specific label incorporated.

9 Claims, No Drawings

NUCLEIC ACID ANALYSIS USING NON-TEMPLATED NUCLEOTIDE ADDITION

CROSS-REFERENCE TO RELATED APPLICATIONS

This application claims the benefit under 35 USC §119(e) of provisional application Ser. No. 60/280,603, filed Mar. 30, 2001, which is incorporated herein by reference.

FIELD OF THE INVENTION

The invention is in the field of molecular biology.

BACKGROUND

The determination of nucleic acid base sequences is important for both research and diagnostics. Many techniques for determining nucleic acid base sequences have been developed over the years, e.g., controlled chemical degradation (Maxim and Gilbert, Proceedings of the National Academy of Sciences USA 74: 560–564 (1977), 2'3' dideoxy chain termination method (Sanger et al. Proceedings of the National Academy of Sciences USA 74: 5463–5467 (1977). A variation of the technique of chain termination sequencing is known as single base extension or "mini-sequencing" is performed when nucleic acid base sequence information is required for only a single base site adjacent to the 3' terminus oligonucleotide primer. The technique of single base extension is described in U.S. Pat. No. 5,856,092 and Syvanen et al. Genomics 8, 684–692 (1990).A problem with single base extension techniques is the difficulty associated with identifying the single base extension product, particularly in an electrophoresis . Variations in the signal produced by the single base extension product, e.g., as detected by an electrophoresis apparatus, maybe the result of variations in signal produced by differences between oligonucleotide primers. The problems associated with identifying single base extension products become particularly troublesome in multiplexed single base extension reactions. The inventors have provided methods, compositions, kits and software for ameliorating these problems associated with identifying single base extension reaction products.

SUMMARY OF CERTAIN EMBODIMENTS OF THE INVENTION

One embodiment of the invention is a method of producing an oligonucleotide extended by a single nucleotide base. An oligonucleotide and an extension terminating nucleotide are mixed with an enzyme having terminal transferase activity. The reaction produces an oligonucleotide extended by a single base. The extended oligonucleotide may be used as a size standard for single base extension reactions.

Another embodiment of the invention is a method of producing a mixture of oligonucleotides extended by different single bases. An oligonucleotide, a first extension terminating nucleotide, and a second extension terminating nucleotide are mixed with an enzyme having terminal transferase activity. The first and second extension terminating nucleotides comprise different nucleotide bases and are labeled with different labels. The identity of the different extension terminating nucleotides (and hence the extended oligonucleotides) may be ascertained by reference to the specific label incorporated. Another embodiment of the invention is a method of identifying the reaction products of single nucleotide base extension reactions on a detection instrument, e.g., an automated fluorescence detecting electrophoresis system, such as an Applied Biosystems PRISM® 377, PRISM® 3700 or PRISM® 3100. An oligonucleotide extension product is produced by mixing an oligonucleotide with an extension terminating nucleotide and an enzyme having terminal transferase activity, e.g., a terminal transferase. The single base oligonucleotide extension product may be used as a standard for comparison with the reaction products of single base extension reactions produced using a DNA polymerase, e.g., a mini-sequencing reaction product. Single base oligonucleotide extension products produced by the enzyme having terminal transferase activity may be resolved on a detection instrument, e.g. an electrophoresis apparatus, so as to produce a signal indicative of the single base extension product standard. The signal may be used as a standard for comparison with signals produced by the reaction products of template-dependent single base extension reaction products.

Other embodiments of the invention are kits for performing one or more methods of the invention. Embodiments of the subject kits include kits that comprise a terminal transferase and one or more extension terminating nucleotides. The extension terminating nucleotides may be labeled with the detectable moieties, such as fluorescent dyes.

DEFINITIONS

The term "terminal transferase" as used herein refers to an enzyme having terminal transferase activity, but not having significant DNA polymerase activity. The term "significant" as used in reference to DNA polymerase activity means DNA polymerase activity sufficient to perform a polynucleotide extension reaction that is template dependent at level sufficient to produce detectable amounts of template-dependent oligonucleotide extension product from an oligonucleotide primed template. Examples of terminal transferases include *E. coli* terminal transferase, calf thymus terminal transferase, and the like. Terminal transferases are commercially available from many companies such as Aphonix, Finnzyrnes, MBI Fernentas, New England Biolabs, Promega, Panvera, Sigma Biochemicals, and Roche Molecular Biochemicals .

The term "terminal transferase activity" as used herein refers to the enzymatic catalysis as of a reaction in which nucleotide triphosphates (including extension terminating nucleotides) are covalently attached to the 3' terminus of an oligonucleotide primer in a template independent manner. Thus, by mixing an enzyme having terminal transferase activity within oligonucleotide having a free 3'-OH (or functional equivalent to) and with a nucleotide triphosphate, one or more nucleotides are added to the 3' prime terminus of the oligonucleotide, irrespective of the presence or absence of a template complementary to the oligonucleotide.

The term "oligonucleotide" as used herein, unless clearly indicated otherwise by context, broadly refers to a polymer of natural or synthetic nucleobases, or a combination of both. The backbone of the capture polynucleotide can be composed entirely of "native" phosphodiester linkages, or it may contain one or modified linkages, such as one or more phosphorothioate, phosphoramidite or other modified linkages. As a specific example, a polynucleotide may be a peptide nucleic acid (PNA), which contains amide interlinkages. Additional examples of modified bases and backbones that can be used in conjunction with the invention, as well as methods for their synthesis can be found, for example, in U.S. Pat. No. 6,001,983; Uhlman & Peyman, 1990, Chemical Review 90(4):544–584; Goodchild, 1990, Bioconjugate Chem. 1(3):165–186; Egholm et al., 1992, J. Am. Chem.

Soc. 114:1895–1897; Gryaznov et al., J. Am. Chem. Soc. 116:3143–3144, as well as the references cited in all of the above. Common modified or synthetic nucleobases of which polynucleotides may be composed include 3-methlyuracil, 5,6-dihydrouracil, 4-thiouracil, 5-bromouracil, 5thorouracil, 5-iodouracil, 6-dimethyl amino purine, 6-methyl amino purine, 2-amino purine, 2,6-diamino purine, 6-amino-8-bromo purine, inosine, 5-methyl cytosine, 7-deazaadenine, and 7-deaza guanosine. Additional non-limiting examples of modified or synthetic nucleobases of which the target nucleic acid may be composed can be found in Fasman, CRC PRACTICAL HANDBOOK OF BIOCHEMISTRY AND MOLECULAR BIOLOGY, 1985, pp. 385–392; Beilstein's Handbuch der Organischen Chemie, Springer Verlag, Berlin and Chemical Abstracts, all of which provide references to publications describing the structures, properties and preparation of such nucleobases. The term "oligonucleotide" as used herein includes oligonucleotides that comprise additional molecules (or atoms) that have been joined, either covalently or non-covalently, to an oligonucleotide. These additional molecules (or atoms) maybe attached to virtually any site on the oligonucleotide, provided the attachment does not prevent the oligonucleotide from being used as a substrate for the enzyme having terminal transferase activity used in a given embodiment of the subject methods. Examples of such additional molecules include mobility modifier compounds such as those described as the subject of U.S. Pat. Nos. 5,514,543, 5,777,096, 5,703,096 and 5,470,705.

The term "extension terminating nucleotide" as used herein refers to refers to an enzymatically-incorporable nucleotide or nucleotide analog in which the sugar moiety does not support incorporation of subsequent nucleotides or nucleotide analogs. Typical terminators are those in which the nucleobase is a purine, a 7-deaza-purine, a pyrimidine, a normal nucleobase or a common analog thereof and the sugar moiety is a pentose which includes a 3'-substituent that blocks further synthesis, such as a ddNTP. Substituents that block further synthesis include, but are not limited to, amino, deoxy, halogen, alkoxy and aryloxy groups. Exemplary terminators include, but are not limited to, those in which the sugar-phosphate ester moiety is 3'-($C_1$–$C_6$)alkylribose-5'-triphosphate, 2'-deoxy-3'-($C_1$–$C_6$)alkylribose-5'-triphosphate, 2'-deoxy-3'-($C_1$–$C_6$)alkoxyribose-5-triphosphate, 2'-deoxy-3'-($C_5$–$C_{14}$)aryloxyribose-5'-triphosphate, 2'-deoxy-3'-haloribose-5'-triphosphate, 2'-deoxy-3'-aminoribose-5'-triphosphate, 2',3'-dideoxyribose-5'-triphosphate or 2',3'-didehydroribose-5'-triphosphate.

The term "detection instrument" as used herein refers to an analytical instrument capable of analyzing polynucleotides based on the size (or weight) of the polynucleotide. Examples of such detection instruments to include, but are not limited to, electrophoresis instruments (included automated DNA sequencers such as the Applied Biosystems ABI PRISM 377, ABI PRISM 310, ABI PRISM 3100, and ABI PRISM 3700) and mass spectragraphs, HPLC, and the like.

The term "resolved" as used herein with respect to a detection instrument refers to detection of a specific signal indicative of a polynucleotide by the instrument. A polynucleotide that is said to be resolved by the instrument may be, but is not necessarily, separated or purified, from other polynucleotides in the mixture.

The term "DNA polymerase" as used herein refers to an enzyme capable of catalyzing in a template dependent manner the addition of nucleotide triphosphates to the 3' terminus of an oligonucleotide that is hybridized to a complementary template.

The term "label" as used, refers to a detectable moiety that maybe attached to a nucleotide in such a way as to permit the addition of the nucleotide (bearing the moiety) to the 3' terminus of an oligonucleotide in a reaction catalyzed by a DNA polymerase. Detectable moieties produce a distinctive signal indicative of the presence of the moiety. Examples of detectable moieties may be fluorescent dyes, chromophores, chemiluminescent compounds, purified isotopes, and the like.

The term "single base extension reaction" (or also "template-dependent single base extension reaction") refers to a method of determining the identity of a nucleotide base at a specific location on a polynucleotide template by extending an oligonucleotide hybridized to the template or single base at the 3' position in a reaction catalyzed by a DNA polymerase. The extension of the oligonucleotide is by only a single base (as opposed to multiple bases) may be achieved by catalyzing the extension in the presence of one or more extension terminating nucleotides and in the absence of extendable nucleotides, e.g., 2' deoxynucleotide triphosphates. The extension terminating nucleotides maybe differentially labeled so as to easily identified which bases been incorporated into the oligonucleotide. Thus, the 3' position is extended by only a single base in a template dependent manner. Another method of achieving single base extension is by adding a single extendable nucleotide so that either extension with a lack of extension is detected. Descriptions of various methods of single base extension reactions can be found in U.S. Pat. No. 5,856,092 and Syvanen et al. Genomics 8, 684–692(1990). The oligonucleotide that has been extended by single base in a single base extension reaction in a template dependent manner (also referred to as "template-dependent single base extension reaction products") is said to be a "single base extension reaction products."

EMBODIMENTS OF THE INVENTION

Several embodiments of the invention relate to the use of terminal transferases (and other enzymes having terminal transferase activity) to produce oligonucleotides extended by a single nucleotide base. These extended oligonucleotide can be used as standards for comparison with template-dependent single base extension reaction products. The extended oligonucleotide produced by the enzyme having terminal transferase activity may be identical to the products of template-dependent single base extension reaction.

One embodiment of the invention is a method of producing an oligonucleotide of interest extended by a single nucleotide base. An oligonucleotide of interest is mixed with one or more extension terminating nucleotides and an enzyme having terminal transferase activity. The enzyme having terminal transferase activity may be a terminal transferase. The extension terminating nucleotides may be labeled or unlabeled. When using more than one extension terminating nucleotides, the different chain terminating nucleotides maybe differentially labeled so as to correspond to different nucleotide bases on the different chain terminating nucleotides, thereby providing a method of conveniently identifying the base on the chain terminating nucleotide that has been incorporated into the oligonucleotide. After mixing, the reaction components mixture is permitted to incubate for an amount of time sufficient to permit the formation of the desired amount of reaction products. Suitable incubation times may be determined through routine experimentation and may vary in accordance with parameters such as the specific enzyme selected, the buffer employed, the reaction component concentrations, reaction temperature, and the like.

Another embodiment invention is a method of producing oligonucleotides extended by a single base in which the oligonucleotide is labeled prior to the addition of an extension terminating nucleotide. A labeled oligonucleotide of interest is mixed with one or more extension terminating nucleotides and an enzyme having terminal transferase activity. The enzyme having terminal transferase activity may be a terminal transferase. The extension terminating nucleotides may be labeled or unlabeled. When using more than one extension terminating nucleotides, the different chain terminating nucleotides maybe differentially labeled so as to correspond to different nucleotide bases on the different chain terminating nucleotides, thereby providing a method of conveniently identifying the base on the chain terminating nucleotide that has been incorporated into the oligonucleotide. After mixing, the reaction components mixture is permitted to incubate for an amount of time sufficient to permit the formation of the desired amount of reaction products. Suitable incubation times may be determined through routine experimentation and may vary in accordance with parameters such as the specific enzyme selected, the buffer employed, the reaction component concentrations, reaction temperature, and the like.

The extended oligonucleotide provided by the methods of the invention may be used as standards for comparison with reaction products of template-dependent single base extension reactions. Meaningful comparisons may obtained by using an enzyme having terminal transferase activity to produce the same reaction product produced in a template-dependent single base extension reaction. The reaction products of the subject methods employing enzymes having terminal transferase activity may easily be designed to be identical to the predicted reaction products of template-dependent single nucleotide base extension reactions. For example, identity of reaction products may be achieved by using the same oligonucleotide and the same chain terminating nucleotides in both reactions. While it is preferable to use standards that are essentially identical to reaction products of template-dependent single nucleotide base extension reactions, it is not necessary to use such identical reaction products.

One example of a need for standards produced by the methods of the invention is in multiplexed template dependent single nucleotide extension reactions that are analyzed when an automated fluorescent nucleic acid analyzer (e.g., an Applied Biosystems 3100). In a multiplexed template dependent single base extension reaction, it may be difficult to identify specific reaction products because of changes in mobility to different labeled extension terminating nucleotides. The reaction products produced by the methods of the invention may be used to mitigate this problem.

In another embodiment of the invention, multiple different oligonucleotide are mixed with one or more different labeled extension terminating nucleotides and an enzyme having terminal transferase activity. This reaction produces multiple different reaction products. The different reaction products can be used as standards for identification of reaction products produced in template-dependent single base extension reactions that employ the same oligonucleotide primers as used to produce the standard.

In addition to employing terminal transferases to catalyze the formation of oligonucleotide extended by a single nucleotide base, the subject methods may use other enzymes having terminal transferase activity. Many DNA polymerases are known to have terminal transferase activity, in embodiments of the invention employing DNA polymerases having terminal transferase activity, it is desirable, but not necessary, to perform the in the non-templated addition in a reaction mixture that lacks significant amounts of template (template as defined with respect to the oligonucleotide primer). By omitting template, template directed addition.

Other embodiments of the invention include kits for producing oligonucleotide that are extended by a single base. The extended oligonucleotides produced using the subject kits are produced in accordance with the methods of the invention employing enzymes having terminal transferase activity. The kits of the invention comprise and enzyme having terminal transferase and an extension terminating nucleotide. The enzyme having terminal transferase activity may a terminal transferase. The kits may comprise one or more different extension terminating nucleotides. The different extension terminating nucleotides may be present in separate solution or maybe present in a single or multiple solution. The kits may also comprise a single solution comprising one or more extension terminating nucleotides and enzyme having terminal transferase activity. The chain extension terminating nucleotides may be labeled.

One example of the kit of the invention is a kit comprising a terminal transferase and four different to chain terminating nucleotides, wearing each nucleotide comprises a different nucleotide base (the four canonical bases A, G, C, and T) and wherein each base is labeled with a different fluorescent dye. The kits are reagents or sets of reagents that are placed in together in a single package unit (or functional equivalent thereof), so as to provide for the convenient practice of the subject methods. Kits may supply the reagents in pre-measured form so as to increased the ease or reproduceability outperforming the subject methods. Kits may contain instructions for performing the subject methods.

The invention, having been described above, may be better understood by reference to the following examples. The examples are offered, for among other reasons, to illustrate specific embodiment of the invention and should not be construed as a limitation on the invention.

EXAMPLES dRhodamine Terminal Transferase Assay

1. Completely thaw Buffer 1, Buffer 2 and dRhodamine Mix on ice.
2. Vortex and spin briefly.
3. Prepare the reaction mix on ice:
   - 4 υl dRhodamine Mix
   - 1 υl Buffer 1
   - 1 υl Buffer 2
   - 1 υl primer (2 υM)
   - 0.1 υl Terminal Transferase
   - 2.9 1 water
   - Total: 10 υl
4. Put the reaction tube in a thermocycler.
   Run conditions:
   - 37° C. for 15 minutes
   - 70° C. for 10 minutes
   - 4° C. hold
5. Add 1 υl Shrimp alkaline phosphatase; mix thoroughly.
6. Put the reaction tube in a thermocycler.
   Run conditions:
   - 37° C. for 60 minutes
   - 72° C. for 15 minutes
   - 4° C. hold 7. Analysis on 3700 DNA Analyzer:
   1). Dilute 1 υl of the final product in 5 υl of formamide.
   2). Mix 1 υl of diluted final product, 0.5 υl of GS120 size standard and 8.5 υl of formamide.
   3). The sample can then be transferred into one well of the 96 well plate and run on 3700 along with SNaPshot products.
8. The final result should show four colored peaks for each primer, with each peak corresponding to the (N+1 ddNTP), which are the same as SNaPshot™ products.

INCORPORATION BY REFERENCE

This application incorporates all publications, patents, and patent application referenced herein in their entirety.

What is claimed is:

1. A method of producing an oligonucleotide extended by a single nucleotide base, said method comprising, mixing an oligonucleotide with a labelled extension terminating nucleotide and a terminal transferase, wherein the oligonucleotide is not coupled to a solid support, thereby forming an oligonucleotide extension product.

2. The method of claim 1, wherein the label is a fluorescent dye.

3. A method of producing an oligonucleotide extended by a single nucleotide base, said method comprising, mixing a labelled oligonucleotide with an extension terminating nucleotide and a terminal transferase, wherein the oligonucleotide is not coupled to a solid support, thereby forming an oligonucleotide extension product.

4. The method of claim 3, wherein the label is a fluorescent dye.

5. A method of producing a mixture of oligonucleotides extended by a single nucleotide base, wherein the mixture comprises oligonucleotides extended by different single bases, said method comprising, mixing an oligonucleotide with a first extension terminating nucleotide, a second extension terminating nucleotide, and a terminal transferase, wherein the first and second extension terminating nucleotides comprise different labels and different nucleotide bases.

6. The method according to claim 5, wherein the labels are fluorescent dyes.

7. A method of producing an oligonucleotide extended by a single nucleotide base, said method comprising, mixing an oligonucleotide with a labelled extension terminating nucleotide and an enzyme having terminal transferase, wherein the mixture does not contain a template that permits the oligonucleotide to function as a primer.

8. A method of producing a mixture of oligonucleotides extended by a single nucleotide base, wherein the mixture comprises oligonucleotides extended by different single bases, said method comprising, mixing an oligonucleotide with a first extension terminating nucleotide, a second extension terminating nucleotide, and an enzyme having terminal transferase activity and an enzyme having terminal transferase activity, wherein the first and second extension terminating nucleotides comprise different labels and different nucleotide bases, wherein the mixture does not contain a template that permits the oligonucleotide to function as a primer.

9. A method of identifying the reaction product of a single nucleotide base extension reaction on a detection instrument, said method comprising, forming a single base oligonucleotide extension product standard by mixing an oligonucleotide with an extension terminating nucleotide and an enzyme having terminal transferase activity, wherein the mixture does not contain a template that permits the oligonucleotide to function as a primer, and resolving the single base oligonucleotide extension product standard on a detection instrument, whereby a signal indicative of the single base oligonucleotide extension product standard is created.

* * * * *